United States Patent
Thompson et al.

(10) Patent No.: US 7,563,519 B2
(45) Date of Patent: *Jul. 21, 2009

(54) OLEDS DOPED WITH PHOSPHORESCENT COMPOUNDS

(75) Inventors: Mark E. Thompson, Anaheim, CA (US); Yujian You, Los Angeles, CA (US); Andrei Shoustikov, Los Angeles, CA (US); Scott Sibley, Baltimore, MD (US); Paul E. Burrows, Princeton Junction, NJ (US); Stephen R. Forrest, Princeton, NJ (US)

(73) Assignees: The Trustees of Frinceton University, Princeton, NJ (US); The University of Southern California, Los Angeles, CA (US)

( * ) Notice: Subject to any disclaimer, the term of this patent is extended or adjusted under 35 U.S.C. 154(b) by 171 days.

This patent is subject to a terminal disclaimer.

(21) Appl. No.: 11/880,676

(22) Filed: Jul. 23, 2007

(65) Prior Publication Data
US 2008/0024058 A1 Jan. 31, 2008

Related U.S. Application Data

(63) Continuation of application No. 11/061,406, filed on Feb. 18, 2005, now abandoned, which is a continuation of application No. 10/426,456, filed on Apr. 30, 2003, now Pat. No. 6,872,477, which is a continuation of application No. 09/900,650, filed on Jul. 6, 2001, now Pat. No. 6,579,632, which is a continuation of application No. 08/980,986, filed on Dec. 1, 1997, now Pat. No. 6,303,238.

(51) Int. Cl.
H01L 51/54 (2006.01)
(52) U.S. Cl. .................. 428/690; 428/917; 313/504; 313/506; 257/E51.041; 257/E51.044
(58) Field of Classification Search .................. None
See application file for complete search history.

(56) References Cited

U.S. PATENT DOCUMENTS

| | | | |
|---|---|---|---|
| 4,950,950 A | 8/1990 | Perry et al. |
| 5,128,587 A | 7/1992 | Skotheim et al. |
| 5,203,974 A | 4/1993 | Kokado et al. |
| 5,231,329 A | 7/1993 | Nishikitani et al. |
| 5,294,810 A | 3/1994 | Egusa et al. |
| 5,457,565 A | 10/1995 | Namiki et al. |
| 5,540,999 A | 7/1996 | Yamamoto et al. |
| 5,554,220 A | 9/1996 | Forrest et al. |
| 5,601,903 A | 2/1997 | Fujii et al. |
| 5,703,436 A | 12/1997 | Forrest et al. |
| 5,707,745 A | 1/1998 | Forrest et al. |
| 5,756,224 A | 5/1998 | Börner et al. |
| 5,757,026 A | 5/1998 | Forrest et al. |
| 5,757,139 A | 5/1998 | Forrest et al. |
| 5,811,833 A | 9/1998 | Thompson |
| 5,834,130 A | 11/1998 | Kido |
| 5,834,893 A | 11/1998 | Bulovic et al. |
| 5,844,363 A | 12/1998 | Gu et al. |
| 5,861,219 A | 1/1999 | Thompson et al. |
| 5,874,803 A | 2/1999 | Garbuzov et al. |
| 5,917,280 A | 6/1999 | Burrows et al. |
| 5,932,895 A | 8/1999 | Shen et al. |
| 5,953,587 A | 9/1999 | Forrest et al. |
| 5,981,306 A | 11/1999 | Burrows et al. |
| 5,986,268 A | 11/1999 | Forrest et al. |
| 5,986,401 A | 11/1999 | Thompson et al. |
| 5,998,803 A | 12/1999 | Forrest et al. |
| 6,013,538 A | 1/2000 | Burrows et al. |
| 6,013,982 A | 1/2000 | Thompson et al. |
| 6,030,715 A | 2/2000 | Thompson et al. |
| 6,045,930 A | 4/2000 | Thompson et al. |
| 6,046,543 A | 4/2000 | Bulovic et al. |
| 6,048,630 A | 4/2000 | Burrows et al. |
| 6,091,195 A | 7/2000 | Forrest et al. |
| 6,097,147 A | 8/2000 | Baldo et al. |
| 6,111,902 A | 8/2000 | Kozlov et al. |
| 6,125,226 A | 9/2000 | Forrest et al. |
| 6,242,115 B1 | 6/2001 | Thomson et al. |
| 6,303,238 B1 | 10/2001 | Thompson et al. |

(Continued)

FOREIGN PATENT DOCUMENTS

DE 44 28 450 2/1996

(Continued)

OTHER PUBLICATIONS

J. Kido, et al., "Electroluminescence in a Terbium Complex", Chemistry Letters, 1990, pp. 657-660.

(Continued)

*Primary Examiner*—Marie R. Yamnitzky
(74) *Attorney, Agent, or Firm*—Kenyon & Kenyon LLP

(57) ABSTRACT

Organic light emitting devices are disclosed which are comprised of a heterostructure for producing electroluminescence wherein the heterostructure is comprised of an emissive layer containing a phosphorescent dopant compound. For example, the phosphorescent dopant compound may be comprised of platinum octaethylporphine (PtOEP), which is a compound having the chemical structure with the formula:

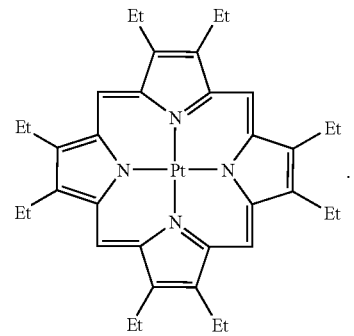

16 Claims, 3 Drawing Sheets

U.S. PATENT DOCUMENTS

| | | | |
|---|---|---|---|
| 6,337,102 B1 | 1/2002 | Forrest et al. | |
| 6,358,631 B1 | 3/2002 | Forrest et al. | |
| 6,413,656 B1 | 7/2002 | Thompson et al. | |
| 6,458,475 B1 | 10/2002 | Adachi et al. | |
| 6,469,437 B1 | 10/2002 | Parthasarathy et al. | |
| 6,524,727 B1 | 2/2003 | Kathirgamanathan | |
| 6,579,632 B2 | 6/2003 | Thompson et al. | |
| 6,645,645 B1 | 11/2003 | Adachi et al. | |
| 6,734,457 B2 | 5/2004 | Yamazaki et al. | |
| 6,803,720 B2 | 10/2004 | Kwong et al. | |
| 6,830,828 B2 | 12/2004 | Thompson et al. | |
| 6,872,477 B2 | 3/2005 | Thompson et al. | |
| 7,279,235 B2 * | 10/2007 | Thompson et al. | 428/690 |
| 7,279,237 B2 * | 10/2007 | Thompson et al. | 428/690 |
| 2003/0146443 A1 | 8/2003 | Yamazaki et al. | |
| 2004/0024425 A1 | 2/2004 | Worley et al. | |
| 2004/0124425 A1 | 7/2004 | Yamazaki et al. | |

FOREIGN PATENT DOCUMENTS

| | | |
|---|---|---|
| EP | 0 704 915 | 4/1996 |
| EP | 0 945 049 | 1/1998 |
| JP | 3-289090 | 12/1991 |
| WO | WO 96/19792 | 6/1996 |
| WO | WO 97/33296 | 9/1997 |
| WO | WO 97/48115 | 12/1997 |
| WO | WO 97/48139 | 12/1997 |
| WO | WO 98/58037 | 12/1998 |

OTHER PUBLICATIONS

J. Kido, et al., "Organic electroluminescent devices using lanthanide complexes", J. Alloys and Compounds, 1993, 192, pp. 30-33.

J. Kido, et al., "Bright red light-emitting organic electroluminescent devices having a europium complex as an emitter", Appl. Phys. Lett., 1994, 65, pp. 2124-2126.

J. Kido, et al., "White-Light-Emitting Organic Electroluminescent Device Using Lanthanide Complexes," Jpn. J. Appl. Phys., 1996, 35, pp. L394-L396.

S. R. Forrest, "Ultrathin Organic Films Grown by Organic Molecular Beam Deposition and Related Techniques," Chemical Reviews, 1997, 97, pp. 1793-1896.

Bulovic et al., "Transparent Light-emitting Devices", Nature 380, 29 (1996).

Whitlock et al., "Investigations of Materials and Device Structures for Organic Semiconductor Solar Cells", Optical Eng., vol. 32., No. 8, 1921-1934 (Aug. 1993).

S.R. Forrest et al., "Organic emitters promise a new generation of displays," Laser Focus World, pp. 99-107, Feb. 1995.

S. Hoshino, et al., "Electroluminescence from triplet excited states of benzophenone", Appl. Phys. Lett. 69 (2), pp. 224-226, Jul. 1996.

C. E. Johnson et al., "Luminescent Iridium (I), Rhodium (I), and Platinum (II) Dithiolate Complexes," 105 *Journal of the American Chemical Society*, pp. 1795-1802, (1983).

Hosokawa et al., "Highly efficient blue electroluminescence from a distyrylarylene emitting layer with a new dopant," *Appl. Phys. Lett.*, 67 (26), pp. 3853-3855 (Dec. 25, 1995).

Adachi et al., , *Jpn. J. Appl. Phys*, 27:L269-L271, Feb. 1988.

Dirr, S. et al., "Vacuum-deposited thin films of lanthanide complexes: spectral properties and applications in OLEDs", SID 97 Digest, pp. 778-781, Soc. for Information Display, Santa Ana, CA, May 1997.

T. Tsutsui et al., "Electroluminescence in Organic Thin Films", *Photochemical Processes in Organized Molecular Systems*, edited by K. Honda, North Holland, Amsterdam, 1991, pp. 437-450.

M. Morikawa et al., "Electrostatic Luminous Cells with the Emitter Layer of Phosphorescent Dyes", Extended Abstracts, The 51st Autumn Meeting of the Japan Society of Applied Physics, 1990, p. 1041, Article 28a-PB-8. *

J. Lee, et al., "Synthesis and Characterization of an Electroluminescent Polyester Containing the Ru(II) Complex", Chem. Mater., 1997, vol. 9, No. 8, pp. 1710-1712.

J.K. Lee, et al., "Thin film light emitting devices from an electroluminescent ruthenium complex", Appl. Phys. Lett. , 69 (12), pp. 1686-1688, Sep. 1996.

D. Yoo, et al., "New Electro-Active Self-Assembled Multilayer Thin Films Based on Alternately Adsorbed Layers of Polyelectrolytes and Functional Dye Molecules", Synthetic Metals, 85, pp. 1425-1426, 1997.

J-K. Lee et al., "Thin Film Light Emitting Heterostructures: From Conjugated Polymers to Ruthenium Complexes to Inorganic Nanocrystallites," Abstracts of Papers, Part 2, 213th ACS National Meeting, American Chemical Society, San Francisco, CA, Apr. 13-17, 1997, No. 200.

Shoustikov, et al., "Orange and red organic light-emitting devices using aluminum tris (5-hydroxyquinoxaline)", Synthetic Metals, vol. 91, May 21, 1997, pp. 217-221.

Wittmann et al., "Optical spectroscopy of platinum and palladium containing poly-ynes", J. Chem. Phys., vol. 101, No. 4, Aug. 15, 1994, pp. 2693-2698.

Zhang et al., "Temperature-dependent electroluminescence from (Eu, Gd) coordination complexes", Appl. Phys. Lett., vol. 71, No. 18, Nov. 3, 1997, pp. 2596-2598.

Y. Ma, et al., "Electroluminescence from triplet metal-ligand charge-transfer excited state of transition metal complexes", Synthetic Metals 94 (1998), pp. 245-248.

M.A. Baldo, et al., "Phosphorescent materials for application to organic light emitting devices", Pure Appl. Chem., vol. 71, No. 11, pp. 2095-2106, 1999.

G. DiMarco, et al., "A Luminescent Iridium(III) Cyclometallated Complex Immobilized in a Polymeric Matrix as a Solid- State Oxygen Sensor", Advanced Materials, vol. 8, pp. 576-580, Jul. 1996.

J.N. Demas, et al., "Design and Applications of Highly Luminescent Transition Metal Complexes", Analytical Chemistry, vol. 63, No. 17, pp. 829-837, Sep. 1, 1991.

K. Vinodgopal, et al., "Photochemistry of Ru(bpy)2(dcbpy)2+ on Al2O3 and TiO2 Surfaces. An Insight into the Mechanism of Photosensitization", J. Phys. Chem. 1995, 99, pp. 10883-10889.

R. Holmlin et al., "Os(phen)2dppz2+ in Photoinduced DNA-Mediated Electron Transfer Reactions", J. Am. Chem. Soc., 118, pp. 5236-5244, 1996.

Chen et al., "Recent Developments in Molecular Organic Electroluminescent Materials" *Macromol. Symp.* 1997, 125, 1-48.

Kolosov et al., "1,8-Naphthalimides in Phosphorescent Organic LEDs: The Interplay between Dopant, Exciplex and Host Emission", *J. Am. Chem. Soc.* 2002, 124 (33), 9945-9954.

Kuwabara et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine(m-MTDATA), as Hole-Transport Materials" *Adv. Mater.* 1994, 6 (9), 677-679.

O'Brien et al., "Improved energy transfer in electrophosphorescent devices" *Appl. Phys. Letts.* 1999, 74 (3) 442-444.

Fujikawa et al., "Energy structures of triphenylamine oligomers" *Synthetic Metals*. 1997, 91, 161-162.

Giro et al. "Multicomponent emission from organic light emitting diodes based on polymer dispersion of an aromatic diamine and an oxadiazole derivative" *Chem. Phys. Letts.* 2000, 318, 137-141.

Makinen et al., "Vacuum level alignment in organic guest-host systems" *J. Appl. Phys*. 2002, 92 (3) 1598-1603.

Gross et al., "Electrogenerated Chemiluminescence from Phosphorescent Molecules Used in Organic Light-Emitting Diodes" *J. Electrochem. Soc*. 2002, 149, E137-E142.

Hopkins et al., "Substituted Aluminum and Zinc Quinolates with Blue-Shifted Absorbance/Luminescence Bands: Synthesis and Spectroscopic, Photoluminescence, and Electroluminescence Characterization", *Chem. Mat.* 1996, 8 (2), 344-351.

C.W. Tang et al., "Organic electroluminescent diodes", *Appl. Phys. Letts*. 1987, 51 (12), 913-915.

Adamovich et al., "New charge-carrier blocking materials for high efficiency OLEDs", *Org. Elect*. 2003, 4, 77-87.

Kanai et al. "Effect of aromatic diamines as cathode interface layer", *Synthetic Metals* 1997, 91, 195-196.

Abkowitz, et al. Chemical Modification of Charge Transport in Silicon Backbone Polymers, Synthetic Metals 1989, 28, 553-558.

Gagne et al. "Ferrocene as an Internal Standard for Electrochemical Measurements", *Inorg. Chem.* 1980, 19, 2854-2855.

Burrows P.E. et al. "Color-Tunable Pixels and Lasers Using Vacuum-Deposited Organic Thin Films" *SPIE*, Jul. 1997, pp. 252-263.

Burrows P.E. et al. "Achieving Full-Color Organic Light-Emitting Devices for Lightweight, Flat-Panel Displays", *IEEE Transactions on Electron Devices*, vol. 44, No. 8, Aug. 8, 1997.

Burrows P.E. et al. Color-Tunable Organic Light Emitting Devices:, *Lasers and Electro-Optics Society Annual Meeting*, 1996, LEOS 96. IEEE, vol. 1, Nov. 1996, pp. 82-83.

Patent Abstracts of Japan, vol. 1996, No. 8, JP Publication No. 08109373 (Apr. 30, 1996).

Patent Abstracts of Japan, vol. 1998, No. 2, JP Publication No. 09268284 (Oct. 14, 1997).

Koene B. E. et al, "Asymmetric Triaryldiamines as Thermally Stable Hole Transporting Layers for Organic Light-Emitting Devices" *Chemistry of Materials*, vol. 10, No. 8, pp. 2235-2250, 1998.

Baldo et al., Nature, 1998, 395: 151-154.

Tang, Ching, SPIE's OE Magazine, p. 19, Feb. 2001.

Gu et al., "High External Quantum Efficiency Organic Light Emitting Devices" Optics Letters, 22(6): Figure 1 and p. 397. Mar. 1997.

Greenham et al., "Angular Dependence of the Light Emission from a Conjugated Polymer Light-Emitting Diode: Implications for Efficiency Calculations", Adv. Materials 1994, 6(6): 491-494.

\* cited by examiner

OLEDS DOPED WITH PHOSPHORESCENT COMPOUNDS

CROSS-REFERENCE TO RELATED APPLICATION

This application is a continuation of U.S. Ser. No. 11/061,406, filed Feb. 18, 2005, now abandoned, which is a continuation of U.S. Ser. No. 10/426,456 filed Apr. 30, 2003, now U.S. Pat. No. 6,872,477, which is a continuation of U.S. Ser. No. 09/900,650 filed Jul. 6, 2001, now U.S. Pat. No. 6,579,632, which is a continuation of U.S. Ser. No. 08/980,986, filed Dec. 1, 1997, now U.S. Pat. No. 6,303,238.

GOVERNMENT RIGHTS

This invention was made with Government support under Contract No. F33615-94-1-1414 awarded by DARPA. The government has certain rights in this invention.

RESEARCH AGREEMENTS

The claimed invention was made by, on behalf of, and/or in connection with one or more of the following parties to a joint university corporation research agreement: Princeton University, The University of Southern California, and the Universal Display Corporation. The agreement was in effect on and before the date the claimed invention was made, and the claimed invention was made as a result of activities undertaken within the scope of the agreement.

BACKGROUND OF THE INVENTION

Organic light emitting devices (OLEDs) are comprised of several organic layers in which one of the layers is comprised of an organic material that can be made to electroluminesce by applying a voltage across the device, C. W. Tang et al., *Appl. Phys. Lett* 51, 913 (1987). Certain OLEDs have been shown to have sufficient brightness, range of color and operating lifetimes for use as a practical alternative technology to LCD-based full color flat-panel displays (S. R. Forrest, P. E. Burrows and M. E. Thompson, Laser Focus World, Feb. 1995). Since many of the thin organic films used in such devices are transparent in the visible spectral region, they allow for the realization of a completely new type of display pixel in which red (R), green (G), and blue (B) emitting OLEDs are placed in a vertically stacked geometry to provide a simple fabrication process, a small R-G-B pixel size, and a large fill factor, International Patent Application No. PCT/US95/15790.

A transparent OLED (TOLED), which represents a significant step toward-realizing high resolution, independently addressable stacked R-G-B pixels, was reported in International Patent Application No. PCT/US97/02681 in which the TOLED had greater than 71% transparency when turned off and emitted light from both top and bottom device surfaces with high efficiency (approaching 1% quantum efficiency) when the device was turned on. The TOLED used transparent indium tin oxide (ITO) as the hole-injecting electrode and a Mg—Ag-ITO electrode layer for electron-injection. A device was disclosed in which the ITO side of the Mg—Ag-ITO electrode layer was used as a hole-injecting contact for a second, different color-emitting OLED stacked on top of the TOLED. Each layer in the stacked OLED (SOLED) was independently addressable and emitted its own characteristic color. This colored emission could be transmitted through the adjacently stacked, transparent, independently addressable, organic layer or layers, the transparent contacts and the glass substrate, thus allowing the device to emit any color that could be produced by varying the relative output of the red and blue color-emitting layers.

The PCT/US95/15790 application disclosed an integrated SOLED for which both intensity and color could be independently varied and controlled with external power supplies in a color tunable display device. The PCT/US95/15790 application, thus, illustrates a principle for achieving integrated, full color pixels that provide high image resolution, which is made possible by the compact pixel size. Furthermore, relatively low cost fabrication techniques, as compared with prior art methods, may be utilized for making such devices.

Such devices whose structure is based upon the use of layers of organic optoelectronic materials generally rely on a common mechanism leading to optical emission. Typically, this mechanism is based upon the radiative recombination of a trapped charge. Specifically, OLEDs are comprised of at least two thin organic layers separating the anode and cathode of the device. The material of one of these layers is specifically chosen based on the material's ability to transport holes, a "hole transporting layer" (HTL), and the material of the other layer is specifically selected according to its ability to transport electrons, an "electron transporting layer" (ETL). With such a construction, the device can be viewed as a diode with a forward bias when the potential applied to the anode is higher than the potential applied to the cathode. Under these bias conditions, the anode injects holes (positive charge carriers) into the hole transporting layer, while the cathode injects electrons into the electron transporting layer. The portion of the luminescent medium adjacent to the anode thus forms a hole injecting and transporting zone while the portion of the luminescent medium adjacent to the cathode forms an electron injecting and transporting zone. The injected holes and electrons each migrate toward the oppositely charged electrode. When an electron and hole localize on the same molecule, a Frenkel exciton is formed. Recombination of this short-lived state may be visualized as an electron dropping from its conduction potential to a valence band, with relaxation occurring, under certain conditions, preferentially via a photoemissive mechanism. Under this view of the mechanism of operation of typical thin-layer organic devices, the electroluminescent layer comprises a luminescence zone receiving mobile charge carriers (electrons and holes) from each electrode.

The materials that produce the electroluminescent emission are frequently the same materials that function either as the electron transporting layer or as the hole transporting layer. Such devices in which the electron transporting layer or the hole transporting layer also functions as the emissive layer are referred to as having a single heterostructure. Alternatively, the electroluminescent material may be present in a separate emissive layer between the hole transporting layer and the electron transporting layer in what is referred to as a double heterostructure.

In addition to emissive materials that are present as the predominant component in the charge carrier layer, that is, either in the hole transporting layer or in the electron transporting layer, and that function both as the charge carrier material as well as the emissive material, the emissive material may be present in relatively low concentrations as a dopant in the charge carrier layer. Whenever a dopant is present, the predominant material in the charge carrier layer may be referred to as a host compound or as a receiving compound. Materials that are present as host and dopant are selected so as to have a high level of energy transfer from the host to the dopant material. In addition, these materials need to be capable of producing acceptable electrical properties for the OLED. Furthermore, such host and dopant materials are preferably capable of being incorporated into the OLED using starting materials that can be readily incorporated into the OLED by using convenient fabrication techniques, in particular, by using vacuum-deposition techniques.

It is desirable for OLEDs to be fabricated using materials that provide electroluminescent emission in a relatively narrow band centered near selected spectral regions, which correspond to one of the three primary colors, red, green and blue so that they may be used as a colored layer in an OLED or SOLED. It is also desirable that such compounds be capable of being readily deposited as a thin layer using vacuum deposition techniques so that they may be readily incorporated into an OLED that is prepared entirely from vacuum-deposited organic materials.

Co-pending U.S. App. Ser. No. 08/774,087, filed Dec. 23, 1996, now U.S. Pat. 6,048,630, is directed to OLEDs containing emitting compounds that produce a saturated red emission. The emission layer is comprised of an emitting compound having a chemical structure represented by Formula I:

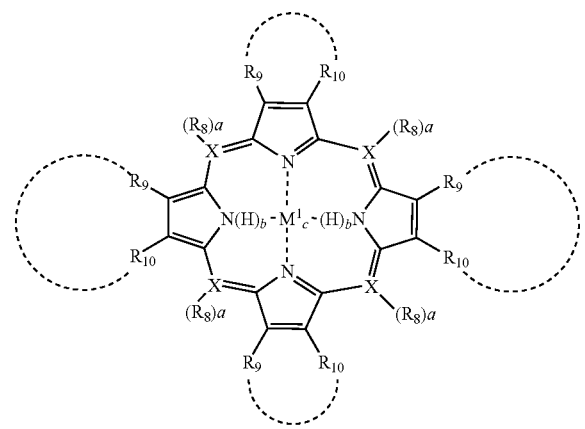

I wherein X is C or N;

$R_8$, $R_9$ and $R_{10}$ are each independently selected from the group consisting of hydrogen, alkyl, substituted alkyl, aryl and substituted aryl; wherein $R_9$ and $R_{10}$ may be combined together to form a fused ring;

$M_1$ is a divalent, trivalent or tetravalent metal; and a, b and c are each 0 or 1;

wherein, when X is C, then a is 1; when X is N, then a is 0; when c is 1, then b is 0; and when b is 1, c is 0.

The examples disclosed in Ser. No.: 08/774,087, filed Dec. 23, 1996, now U.S. Pat. 6,048,630 included an emissive compound of Formula I wherein X=C, R8=phenyl; R9=R10=H; c=0; and b=1. This compound has the chemical name 5,10, 15,20-tetraphenyl-21H,23H-porphine (TPP). OLEDs comprised of the TPP-containing emissive layer produce an emission spectrum comprised of two narrow bands that are centered at about 650 and about 713 nm, as shown in FIG. 1. The emission from this device involves fluorescence from the TPP dopant. One of the problems with the TPP-doped device is that the narrow band at 713 nm, which comprises about 40% of the emission, is not within a range that is useful for display applications. A second problem is that TPP-doped OLEDs are very unstable, such that the shelf life of such devices is typically very short. It would be desirable if these two aspects of TPP-doped devices could be improved. The present invention is directed to addressing these problems of prior art devices.

Another aspect of the present invention relates to the fact that, based on spin statistical arguments, it is generally understood that the majority of the excitons that are produced in an OLED are in a non-emissive triplet electronic state. Formation of such triplet states can result in a substantial loss of the excitation energy in the OLED via radiationless transitions to the ground state. It would be desirable if the total OLED quantum efficiency could be enhanced by utilizing this energy transfer pathway through the exciton triplet states, for example, by having the exciton triplet state energy transferred to an emissive material. Unfortunately, though it is known that the energy from an excited triplet state may be efficiently transferred under certain circumstances to the triplet state of a molecule that phosphoresces, the phosphorescent decay rate is typically not expected to be rapid enough to be adequate for use in a display device.

The present invention is further directed to OLEDs which also address such problems of prior art devices.

ADVANTAGES AND SUMMARY OF THE INVENTION

The present invention is directed to OLEDs, and a method of fabricating OLEDs, in which emission from the device is obtained via a phosphorescent decay process wherein the phosphorescent decay rate is rapid enough to meet the requirements of a display device.

More specifically, the present invention is directed to OLEDs comprised of a material that is capable of receiving the energy from an exciton singlet or triplet state and emitting that energy as phosphorescent radiation.

One of the benefits of the present invention is that the phosphorescent decay process utilizes exciton triplet state energy that is typically wasted in an OLED via a radiationless energy transfer and relaxation process.

The present invention is further directed to OLEDs that are capable of producing a highly saturated red emission. More specifically, OLEDs of the present invention are comprised of platinum octaethylporphine (PtOEP), a compound that produces a narrow emission band that peaks near 640 nm when the PtOEP is doped in an electron transporting layer comprised of tris-(8-hydroxyquinoline)-aluminum ($Alq_3$). Such emission is perceived as highly saturated red emission Another of the benefits of PtOEP-doped LEDs is that such OLEDs have a stability, when the device is exposed to ambient environmental conditions for a few days, that is comparable to prior art devices and, in particular, a decidedly greater shelf life stability as compared with TPP-doped devices.

Further objectives and advantages of the present invention will be apparent to those skilled in the art from the detailed description of the disclosed invention.

DETAILED DESCRIPTION OF THE PREFERRED EMBODIMENTS

The present invention will now be described in detail for specific preferred embodiments of the invention, it being understood that these embodiments are intended only as illustrative examples and the invention is not to be limited thereto.

The present invention is directed to OLEDs in which emission from the device is obtained via a phosphorescent decay process wherein the phosphorescent decay rate is rapid enough to meet the requirements of a display device. As a representative embodiment of the present invention the emission layer is comprised of an emitting compound having a structure represented by Formula I:

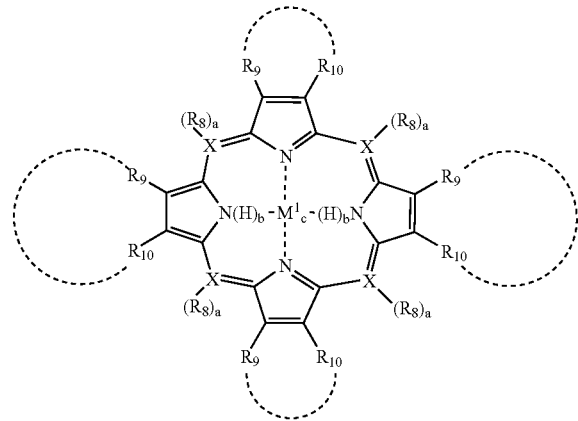

I wherein M=Pt; a=1; b=0; c=1; X=C; and $R_8$=H; and $R_9$=$R_{10}$=Et (ethyl). In particular, this compound, platinum octaethylporphine (PtOEP), has the chemical structure of formula II:

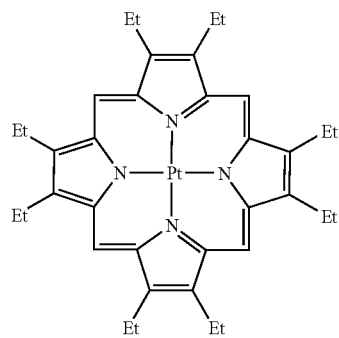

II

The advantage of selecting a dopant compound such as PtOEP as the emissive material of an OLED is based, inter alia, on two particular facts. First, the photoluminescent quantum yield for this molecule is significantly greater than TPP, PtOEP having a photoluminescent quantum yield of greater than 50%, and as high as 90% in the solid state, and TPP having a photoluminescent quantum yield of only about 10%. The improved photoluminescent quantum yield makes it possible to fabricate OLEDs with increased efficiencies. A second advantage that is offered by selecting a phosphorescent compound such as PtOEP is that the emission from such a molecule comes from a triplet state. A molecule that is capable of being excited to a triplet state provides the possibility of having the energy transferred from the non-emissive exciton triplet state to a triplet state that is capable of radiatively emitting this energy as phosphorescent radiation. Though phosphorescence, which refers to radiation that comes from a triplet state, typically occurs at a much slower rate than fluorescence, which refers to radiation from a singlet state, the phosphorescence from a compound such as PtOEP is, nevertheless, sufficiently rapid to satisfy the requirements of certain display devices. In particular, a compound such as PtOEP, which has a lifetime of about 7 μsec when used as the dopant in an Alq₃ layer, may be used in passive matrix displays that require a switching time of not faster than about 10 μsec or in an active matrix display for which the switching time only needs to be about 10 msec.

Figure 1:
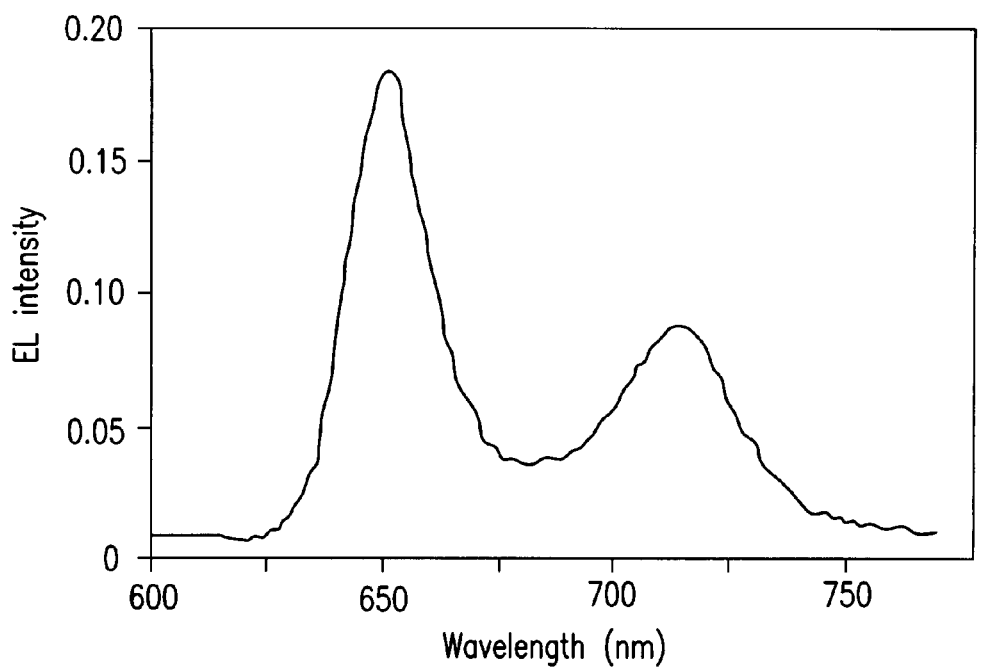
FIG. 1 shows the electroluminescent (EL) spectrum of TPP-doped OLEDs.
Figure 2:
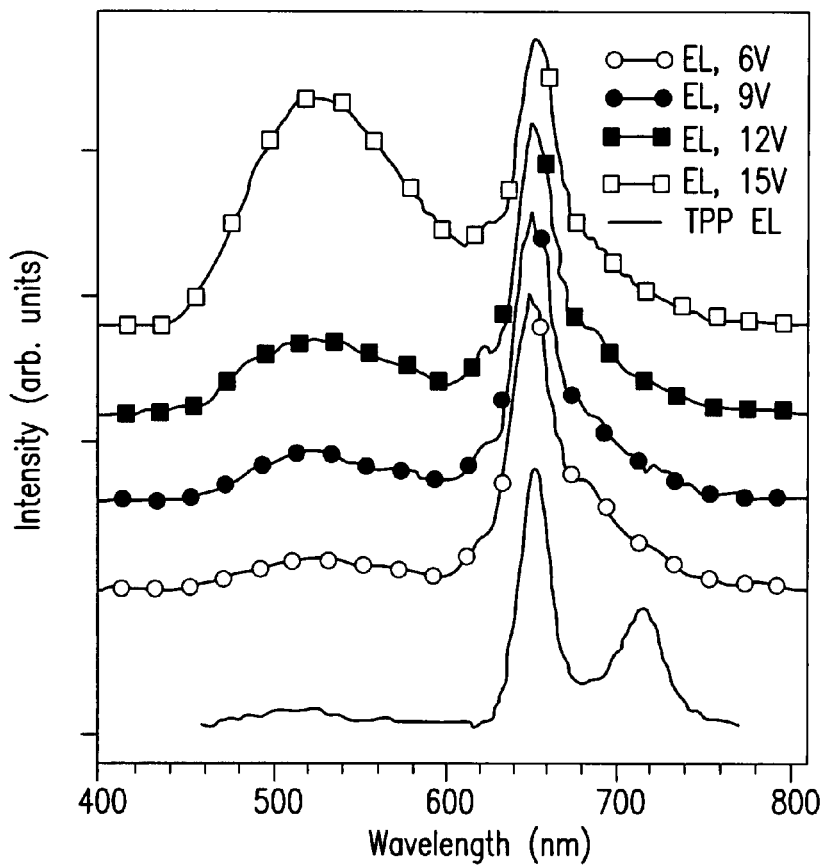
FIG. 2 shows the EL spectra as a function of wavelength at different voltages (6, 9, 12 and 15V) for OLEDs having an $Alq_3$ layer doped with 0.6 mol % PtOEP as compared with the EL spectrum of a TPP-doped device ("TPP EL").
Figure 3:
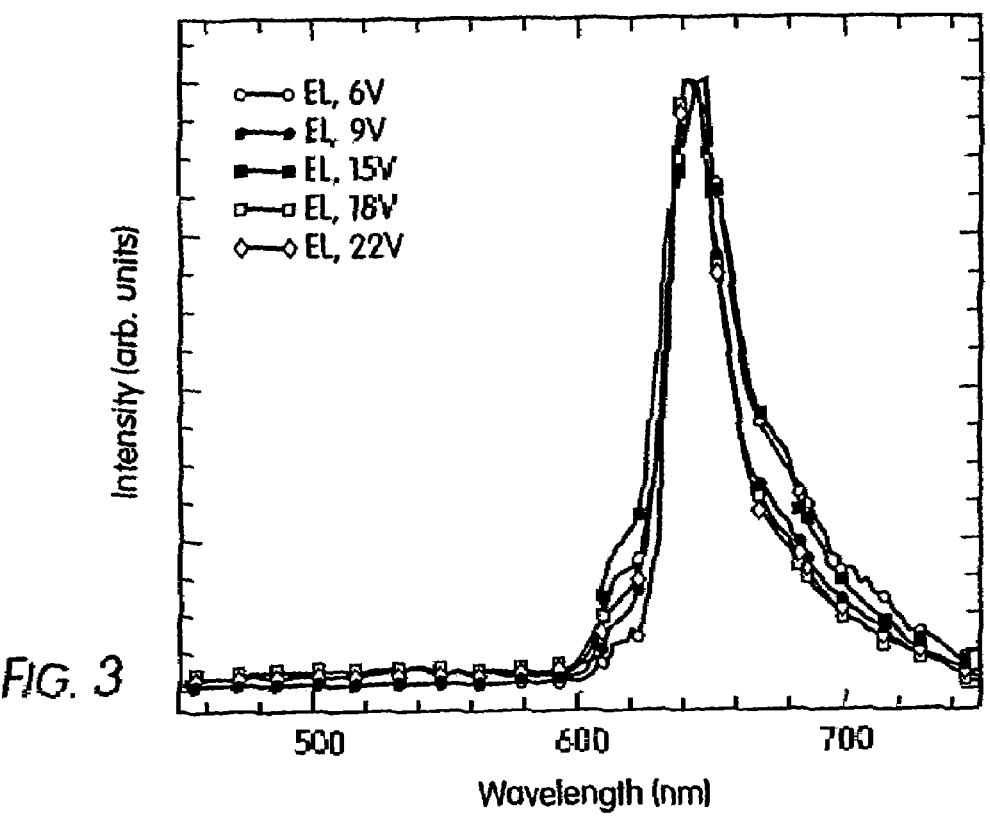
FIG. 3 shows the EL spectra as a function of wavelength at different voltages for OLEDs doped with about 6 mol % PtOEP.

As a representative embodiment of the present invention, the PtOEP may be doped into the Alq₃ layer of an ITO/TPD/Alq₃/Mg—Ag OLED. The behavior of such PtOEP-doped OLEDs is very different from OLEDs prepared with TPP dopants. At doping levels greater than 0.5 mol % TPP, the emission from the OLED is exclusively from the TPP. In contrast, at low to moderate doping levels of PtOEP in Alq₃, the emission is dominated by PtOEP emission at low voltage, but as the voltage is increased, Alq₃ emission appears. At moderately high voltages (e.g., 15 V) the majority of the emission comes from Alq₃. The EL spectra for a 0.6 mol % PtOEP doped OLED are given in FIG. 2. The spectra for 1.3 mol % PtOEP have about the same shape as those shown for the 0.6 mol % device. The shape of the spectra of an OLED prepared with 6 mol % PtOEP are shown in FIG. 3. As the voltage is increased, the intensity of the red emission increases significantly, but a contribution from Alq₃ emission is not observed, even at a high voltage.

While the present invention is not limited by the theory of how it works, it is believed that the explanation for the increase in Alq₃ emission as the voltage is increased is related to the different lifetimes for photoluminescence for Alq₃ and PtOEP. The PL lifetime for Alq₃ is about 13 nsec (nanoseconds) in both the solid state and in solution, whereas the PL lifetime of PtOEP varies from about 10 to about 100 μsec (microseconds) depending on the medium. If the voltage applied to the PtOEP-doped device is kept low, the number of excitons transferred to PtOEP is small enough such that the excited PtOEP molecules can relax at a sufficient rate relative to the Alq₃ exciton creation rate, with the result that there are always enough dopant molecules for energy transfer from the Alq₃. As the voltage is increased, the available PtOEP dopant molecules become saturated and cannot relax fast enough to keep up with the rate at which the excitons are being created in the Alq₃. In this higher voltage regime, some of the Alq₃ excitons relax by radiative emission before the excitation energy can be transferred to the PtOEP molecules. At 6 mol % PtOEP, enough dopant is present to trap all of the excitons, but the higher doping levels lead to decreased overall efficiency.

Figure 4:
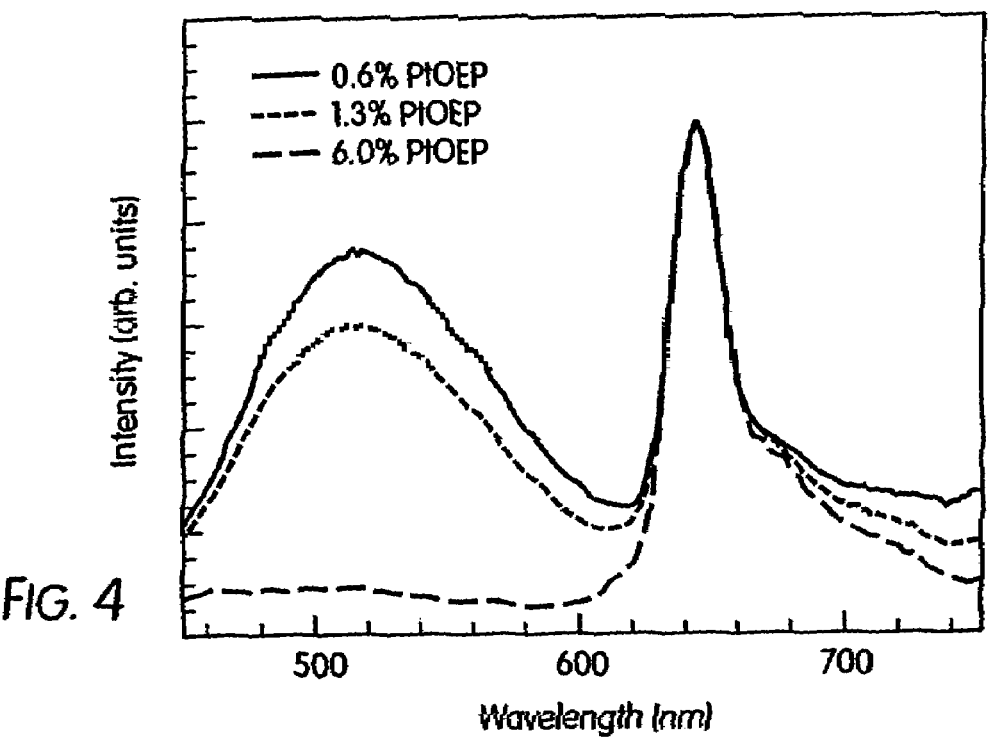
FIG. 4 shows the photoluminescent (PL) spectra as a function of wavelength for different PtOEP concentrations for Alq₃ devices doped with PtOEP.

This explanation is further supported by the results shown in FIG. 4, which show the PL spectra as a function of wavelength at different doping levels for PtOEP-doped Alq$_3$ devices. At the lowest doping levels of 0.6 mol %, a large emission band characteristic of Alq$_3$ is observed, whereas for the high 6 mol % PtOEP-doping level, there appears to be sufficient PtOEP present to capture all the exciton energy from the Alq$_3$.

Figure 5:
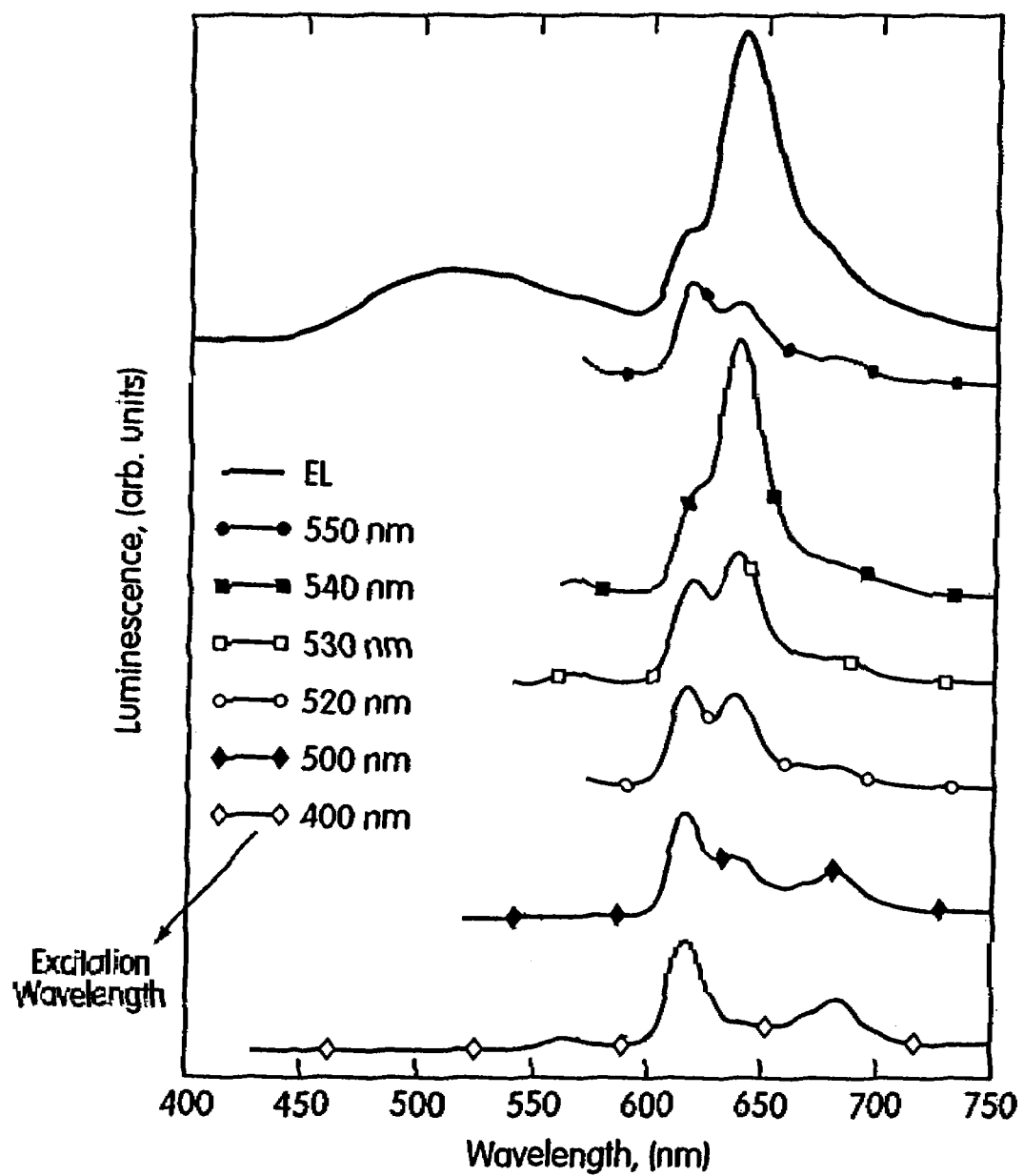
FIG. 5 shows the PL spectra as a function of wavelength at different excitation wavelengths for a solution of PtOEP as compared with the EL spectrum of an OLED having an Alq₃ layer doped with 0.6 mol % PtOEP.

The emission from the PtOEP-based OLEDs is very narrow and centered at 645 nm. This narrow band, which corresponds to saturated red emission, has a full width at half maximum of about 30 nm. A comparison of the PL spectra as a function of wavelength at different excitation-wavelengths for PtOEP in solution, as shown in FIG. 5, with the EL spectrum of a PtOEP-doped Alq$_3$ OLED, shows that a PtOEP-doped OLED selectively produces the narrow band of emission from PtOEP that is centered with a peak at about 645 nm. This narrow, highly saturated red emission is produced, with almost the total absence of the other PtOEP peaks, even though a comparison of the PL excitation spectrum of PtOEP with the broad emission band from the Alq$_3$ might lead one to expect additional bands centered at about 620 and about 685 nm, as is observed for the PL spectra of PtOEP in solution.

The net result is that the emission from a PtOEP-doped device is significantly better, with respect to the saturated red emission, than that of a TPP-doped device since there is no long wavelength tail or peak above 700 nm. The quantum efficiencies for these devices, which are external quantum yields, are listed in Table 1. In each case, the efficiency is listed along with that of a reference device (ITO/TPD/Alq$_3$/Mg—Ag) prepared in parallel with the doped device. At low drive voltages, the efficiencies of the doped devices are superior, while at higher voltages the undoped device has a higher efficiency. These results show that PtOEP-doped devices are capable of performing with efficiencies comparable to prior art Alq$_3$-doped devices.

The shelf lives of PtOEP devices that were exposed to ambient environmental conditions for a few days were observed to be comparable to undoped Alq$_3$ devices and decidedly superior to devices prepared with TPP as the dopant.

TABLE 1

External quantum efficiencies for PtOEP-doped Alq$_3$ OLEDs as compared with an undoped Alq$_3$ OLED reference.

| Conc. | Voltage | n (doped) | n (ref.) |
| --- | --- | --- | --- |
| 0.6 mol % | low volt (6-7 V) | 0.2% | 0.15% |
|  | high volt (11-12 V) | 0.07% | 0.18% |
| 1.3 mol % | low volt (6-7 V) | 0.2% | 0.11% |
|  | high volt (11-12 V) | 0.11% | 0.24% |
| 6 mol % | low volt (6-7 V) | 0.14% | 0.17% |
|  | high volt (11-12 V) | 0.07% | 0.2% |

Such OLEDs may be used, for example, in passive matrix flat panel displays having a switching time not faster than about 10 μsec, in active matrix displays for which the switching time only needs to be about 10 msec, or in low resolution display applications. The phosphorescent compounds may be selected, for example, from those phosphorescent compounds which have the chemical structure of formula I:

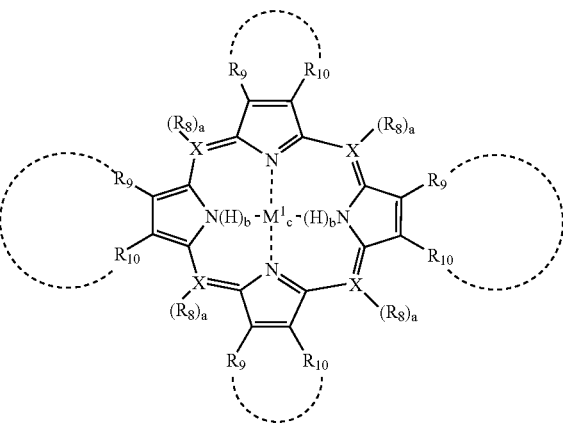

wherein X is C or N;

R$_8$, R$_9$ and R$_{10}$ are each independently selected from the group consisting of hydrogen, alkyl, substituted alkyl, aryl and substituted aryl;

R$_9$ and R$_{10}$ may be combined together to form a fused ring;

M$_1$ is a divalent, trivalent or tetravalent metal; and a, b and c are each 0 or 1;

wherein, when X is C, then a is 1; when X is N, then a is 0; when c is 1, then b is 0; and when b is 1, c is 0.

The phosphorescent compounds may also be selected, as another example, from phosphorescent porphyrin compounds, which may be partly or fully hydrogenated.

In addition to selecting phosphorescent compounds according to their phosphorescent lifetimes, which for certain applications may mean selecting compounds having a phosphorescent lifetime not longer than about 10 μsec, the phosphorescent compounds may be selected according to their ability to effectively capture the exciton triplet energy from a charge carrier material and then to emit that excitation energy as phosphorescence in a narrow emission band corresponding to a highly saturated color, such as demonstrated by PtOEP in an Alq$_3$-based OLED.

A dopant capable of shifting the emission wavelength of an emissive layer comprised only of a host compound is added to the host compound in an amount effective to shift the wavelength of emission so that the LED device preferably emits light that is perceived by the human eye to be close to one of the primary colors. Although it is recognized that characterization of color perception is a subjective exercise, a quantitative chromaticity scale has been developed by the Commission Internationale de l'Eclairage (International Commission of Illumination), otherwise known as the CIE standard. According to this standard, a saturated color may be represented by a single point, with specific quantitative coordinates according to the defined axes of the chromaticity scale. It will be appreciated by one of skill in the art that such a single point on the CIE scale would represent a standard or a goal that, in practical terms, is difficult, but fortunately, unnecessary, to attain.

In the preferred embodiments of the present invention in which the OLED predominantly produces a primary color, the dopant is incorporated into a host compound so that the OLED emits light that is perceived by the human eye to be close to a saturated primary color. Through the practice of the present invention, it is intended that OLEDs be constructed which can be characterized by an emission that is close to an absolute (or saturated) chromaticity value, as that would be defined by the CIE scale. Furthermore, LED's utilizing the materials of the present invention are also intended to be capable of a display brightness that can be in excess of 100 cd/m$^2$ although somewhat lower values, perhaps as low as 10 cd/m$^2$, may be acceptable in certain cases.

The host compounds as defined herein are compounds which can be doped with dopants that emit light with the desired spectral characteristics. Such compounds include, but are not limited to, the emitting compounds and host compounds as described in U.S. patent application Ser. No. 08/693,359, filed 6 Aug. 1996, now U.S. Pat. No. 6,358,631, incorporated herein by reference. The term "host" is used to refer to the compound in the emissive layer that functions as the component, that is, "receiving compound" which receives the hole/electron recombination energy and then by an emission/absorption energy transfer process, transfers that excitation energy to the dopant compound, which is typically present in much lower concentrations. The dopant may then relax to an excited state having a slightly lower energy level, which preferentially radiates all of its energy as luminescent emission in a desired spectral region. A dopant that radiates 100% of the dopant's excited state excitation energy is said to have a quantum efficiency of 100%. For host/dopant concentrations which are to be used in a color tunable SOLED, preferably most, if not all, of the host's excitation energy is transferred to the dopant which in turn radiates, perhaps from a lower energy level, but with a high quantum efficiency, to produce visible radiation having a desired chromaticity. The present invention is directed toward phosphorescent compounds that are intended to serve as dopants which satisfy these demanding energy transfer requirements.

As the term host compound is used herein, it will be appreciated that such compounds can be found in an electron transporting/emissive layer or a hole transporting/emissive layer of a single heterostructure OLED device or in the separate emissive layer of a double heterostructure device. As will be recognized by one of skill in the art, use of the dopant species such as disclosed herein makes it possible to extend not only the range of colors emitted by the OLED, but also to extend the range of possible candidate species for host and/or dopant compounds. Accordingly, for effective host/dopant systems, although the host compound can have a strong emission in a region on the spectrum where the dopant species strongly absorbs light, the host species preferably does not have an emission band in a region where the dopant also emits strongly. In structures where the host compound also functions as a charge carrier, then additional criteria such as redox potential for the species also becomes a consideration. In general, however, the spectral characteristics of the host and dopant species are the most important criteria.

The amount of dopant that is present is that amount which is sufficient to shift the emission wavelength of the host material as close as possible to a saturated primary color, as that would be defined according to the CIE scale. Typically, the effective amount is from about 0.01 to 10.0 mol %, based on the emitting layer. The primary criterion for determining an appropriate doping level is the level which is effective for achieving an emission with the appropriate spectral characteristics. By way of example, and without limitation, if the amount of dopant species is at too low a level, then emission from the device will also comprise a component of light from the host compound itself, which will be at shorter wavelengths than the desired emission form the dopant species. In contrast, if the level of dopant is too high, emission efficiencies could be adversely affected by self-quenching, a net non-emissive mechanism. Alternatively, too high levels of the dopant species could also adversely affect the hole or electron transporting properties of the host material.

The OLEDs of the present invention are comprised of a heterostructure for producing electroluminescence which may be fabricated as a single heterostructure or as a double heterostructure. The materials, methods and apparatus for preparing the organic thin films of a single or double heterostructure are disclosed, for example, in U.S. Pat. No. 5,554,220, which is incorporated herein in its entirety by reference. As used herein, the term "heterostructure for producing electroluminescence" refers to a heterostructure that includes, for a single heterostructure, in sequence, a hole injecting anode layer, a hole transporting layer, an electron transporting layer, and a cathode layer. An additional layer or layers may be present between one or more of the sequential pairs of these layers. For example, for a double heterostructure, a separate emissive layer is included between the hole transporting layer and the electron transporting layer. This separate emissive layer may be characterized as being a "thin luminescent layer." Alternatively, or in addition, a hole injection enhancement layer may be present between the anode layer and the hole transporting layer and/or an electron injecting and interface layer may be present between the cathode layer and the electron transporting layer.

Either the anode layer or the cathode layer may be in contact with a substrate and each electrode is connected to electrical contacts which are capable of delivering a voltage across the device causing it to produce electroluminescence from an electron transporting layer, a hole transporting layer or a separate emissive layer. If the cathode layer is deposited on the substrate, the device may be referred to as having an inverted OLED (IOLED) structure. An inverted structure may also be referred to as an "OILED" structure. If the heterostructure for producing electroluminescence is included as part of a stacked OLED. (SOLED), one or both of the electrodes of an individual heterostructure may be in contact with an electrode of an adjacent heterostructure. Alternatively, dependent on the circuitry used to drive the SOLED, an insulating layer may be provided between the adjacent electrodes of the OLEDs in the stack.

The single or double heterostructures as referred to herein are intended solely as examples for showing how an OLED embodying the present invention may be fabricated without in any way intending the invention to be limited to the particular materials or sequence for making the layers shown. For example, a single heterostructure typically includes a substrate which may be opaque or transparent, rigid or flexible, and/or plastic, metal or glass; a first electrode, which is typically a high work function, hole-injecting anode layer, for example, an indium tin oxide (ITO) anode layer; a hole transporting layer; an electron transporting layer; and a second electrode layer, for example, a low work function, electron-injecting, metal cathode layer of a magnesium-silver alloy, (Mg:Ag) or of a lithium-aluminum alloy, (Li:Al). Alternatively, as disclosed in the application entitled "A Highly Transparent Organic Light Emitting Device Employing on a Non-Metallic Cathode", Ser. No. 08/964,863, filed Nov. 5, 1997, now U.S. Pat. No. 6,469,437, which is incorporated in its entirety by reference, the cathode may be a non-metallic material such a ITO, the term "non-metallic" being used to embrace still other transparent conducting inorganic layers, as well as materials comprised of metals that may be present as one of the elements in a chemical compound, for example, as an oxide. However, the term "non-metallic" does not embrace materials comprised predominantly of the free metal nor does the term embrace metal alloys.

Materials that may be used as the substrate in a representative embodiment of the present invention include, in particular, glass, transparent polymer such as polyester, sapphire or quartz, or substantially any other material that may be used as the substrate of an OLED.

Materials that may be used as the hole-injecting anode layer in a representative embodiment of the present invention include, in particular, ITO, Zn—In—SnO$_2$ or SbO$_2$, or substantially any other material that may be used as the hole-injecting anode layer of an OLED.

Materials that may be used in the hole transporting layer in a representative embodiment of the present invention include, in particular, N,N'-diphenyl-N,N'-bis(3-methylpheny)1-1'biphenyl-4,4'diamine (TPD), 4,4'-bis[N-(1-naphthyl)-N-phenyl-amino]biphenyl (α-NPD) or 4,4'-bis[N-(2-naphthyl)-N-phenyl-amino]biphenyl (β-NPD).

Materials that may be used as the electron transporting layer include, in particular, tris-(8-hydroxyquinoline)-aluminum (Alq$_3$) and carbazole.

Materials that may be used as the separate emissive layer, if present, include, in particular, dye-doped Alq$_3$, or substantially any other material that may be used as the separate emissive layer of an OLED.

The insulating layer, if present, may be comprised of an insulating material such as SiO$_2$, SiN$_x$ or AlO$_2$, or substantially any other material that may be used as the insulating material of an OLED, which may be deposited by a variety of processes such as plasma enhanced chemical vapor deposition (PECVD), electron beam, etc.

The hole injecting enhancement layer may in some cases be comprised of the same material, CuPc, as is used in the electron injecting and interface layer. In each case, the CuPc layer may be in direct contact with an ITO electrode, with the distinction between the two CuPc layers being that in one case the CuPc layer is in contact with an ITO layer that functions as an anode and in the other case the ITO layer functions as a cathode. In each case, the CuPc layer functions as a charge carrier and interface layer. On the one hand when in contact with the ITO anode, the CuPc layer assists in injecting and transporting holes from the anode to a hole transporting layer, and on the other hand when in contact with the ITO cathode, the CuPc layer assists in injecting and transporting electrons from the cathode to an electron transporting layer. The term "electron injecting interface layer" is used to refer to this layer that is present between and in contact with the cathode layer and the electron transporting layer of the heterostructure. The CuPc layer, in each case, may also function as a protection layer that protects any underlying organic layers, if present, from damage during the ITO deposition process. The protection layer may also be comprised of others materials such a 3,4,9,10-perylenetetra-carboxylic dianhydride (PTCDA). Whenever the ITO layer is present as the electrode in a SOLED structure, opposite faces of the ITO may function as an anode and cathode, respectively.

The OLEDs of the present invention have the advantage that they can be fabricated entirely from vacuum-deposited molecular organic materials as distinct, for example, from OLEDs in which some of the layers are comprised of polymeric materials, which cannot be readily deposited using vacuum deposition techniques. A vacuum-deposited material is one which can be deposited in a vacuum typically having a background pressure less than one atmosphere, preferably about $10^{-5}$ to about $10^{-11}$ torr for vacuum deposition, or about 50 torr to about $10^{-5}$ torr for vapor deposition.

Although not limited to the thickness ranges recited herein, the substrate may be as thin as 10μ, if present as a flexible plastic or metal foil substrate, such as aluminum foil, or substantially thicker if present as a rigid, transparent or opaque, substrate or if the substrate is comprised of a silicon-based display driver; the ITO anode layer may be from about 500 Å (1 Å=$10^{-8}$ cm) to greater than about 4000 Å thick; the hole transporting layer from about 50 Å to greater than about 1000 Å thick; the separate emissive layer of a double heterostructure, if present, from about 50 Å to about 200 Å thick; the electron transporting layer from about 50 Å to about 1000 Å thick; and the metal cathode layer from about 50 Å to greater than about 100 Å thick, or substantially thicker if the cathode layer includes a protective silver layer and is opaque.

Thus, while there may be substantial variation in the type, number, thickness and order of the layers that are present, dependent on whether the device includes a single heterostructure or a double heterostructure, whether the device is a SOLED or a single OLED, whether the device is a TOLED or an IOLED, whether the OLED is intended to produce emission in a preferred spectral region, or whether still other design variations are used, the present invention is directed to those devices in which the OLED is comprised of a heterostructure for producing electroluminescence wherein the heterostructure is comprised of an emissive layer containing a phosphorescent compound.

The subject invention as disclosed herein may be used in conjunction with co-pending applications: "High Reliability, High Efficiency, Integratable Organic Light Emitting Devices and Methods of Producing Same", Ser. No. 08/774,119 (filed Dec. 23, 1996) now U.S. Pat. No. 6,046,543; "Novel Materials for Multicolor Light Emitting Diodes", Ser. No. 08/850,264 (filed May 2, 1997), now U.S. Pat. No. 6,045,930; "Electron Transporting and Light Emitting Layers Based on Organic Free Radicals", Ser. No. 08/774,120 (filed Dec. 23, 1996), now U.S. Pat. No. 5,811,833; "Multicolor Display Devices", Ser. No. 08/772,333 (filed Dec. 23, 1996), now U.S. Pat. No. 6,013,982; "Red-Emitting Organic Light Emitting Devices (OLED's)", Ser. No. 08/774,087 (filed Dec. 23, 1996), now U.S. Pat. No. 6,048,630; "Driving Circuit For Stacked Organic Light Emitting Devices", Ser. No. 08/792,050 (filed Feb. 3, 1997), now U.S. Pat. No. 5,757,139; "High Efficiency Organic Light Emitting Device Structures", Ser. No. 08/772,332 (filed Dec. 23, 1996), now U.S. Pat. No. 5,834,893; "Vacuum Deposited, Non-Polymeric Flexible Organic Light Emitting Devices", Ser. No. 08/789,319 (filed Jan. 23, 1997) now U.S. Pat. No. 5,844,363; "Displays Having Mesa Pixel Configuration", Ser. No. 08/794,595 (filed Feb. 3, 1997), now U.S. Pat. No. 6,091,195; "Stacked Organic Light Emitting Devices", Ser. No. 08/792,046 (filed Feb. 3, 1997), now U.S. Pat. No. 5,917,280; "High Contrast Transparent Organic Light Emitting Device Display", Ser. No. 08/82 1,380 (filed Mar. 20, 1997), now U.S. Pat. No. 5,986,401; "Organic Light Emitting Devices Containing A Metal Complex of 5-Hydroxy-Quinoxaline as A Host Material", Ser. No. 08/838,099 (filed Apr. 15, 1997), now U.S. Pat. No. 5,861,219; "Light Emitting Devices Having High Brightness", Ser. No. 08/844,353 (filed Apr. 18, 1997), now U.S. Pat. No. 6,125,226; "Organic Semiconductor Laser", Ser. No. 08/859,468 (filed May 19, 1997) now U.S. Pat. No. 6,111,902; "Saturated Full Color Stacked Organic Light Emitting Devices", Ser. No. 08/858,994 (filed May 20, 1997), now U.S. Pat. No. 5,932,895; "An Organic Light Emitting Device Containing a Hole Injection Enhancement Layer", Ser. No. 08/865,491 (filed May 29, 1997), now U.S. Pat. No. 5,998, 803; "Plasma Treatment of Conductive Layers", PCT/US97/10252, (filed Jun. 12, 1997); "Patterning of Thin Films for the Fabrication of Organic Multi-color Displays", PCT/US97/10289, (filed Jun. 12, 1997); "OLEDs Containing Thermally Stable Asymmetric Charge Carrier Materials", Ser. No. 98/925,029, (filed Sep. 8, 1997), now U.S. Pat. No. 6,242,115; "Light Emitting Device with Stack of OLEDS and Phosphor Downconverter", Ser. No. 08/925,403, (filed Sep. 9, 1997), now U.S. Pat. No. 5,874,803; "An Improved Method for Depositing Indium Tin Oxide Layers in Organic Light Emitting Devices", Ser. No. 08/928,800 (filed Sep. 12, 1997), now U.S. Pat. No. 5,981,306; "Azlactone-Related Dopants in the Emissive Layer of an Oled"(filed Oct. 9, 1997), Ser. No. 08/948,130, now U.S. Pat. No. 6,030,715; "A Highly Transparent Organic Light Emitting Device Employing A Non-Metallic Cathode", Ser. No. 60/064,005 (filed Nov. 3, 1997), "A Highly Transparent Organic Light Emitting Device Employing a Non-Metallic Cathode", Ser. No. 08/964,863 (filed Nov. 5, 1997), now, U.S. Pat. No. 6,469,43; "Low Pressure Vapor Phase Deposition of Organic Thin Films" (filed Nov. 17, 1997), Ser. No. 08/972,156, now U.S. Pat. No. 6,337,102; "Method of Fabricating and Patterning Oleds", (filed Nov. 24, 1997), Ser. No. 08/977,205, now U.S. Pat. No. 6,013,538 and "Method for Deposition and Patterning of Organic Thin Film", (filed Nov. 24, 1997), Ser. No. 08/976,666, now U.S. Pat. No. 5,953,587; each co-pending application being incorporated herein by reference in its entirety. The subject invention may also be used in conjunction with the subject matter of each of co-pending U.S. patent application Ser. No. 08/354,674, now U.S. Pat. No. 5,707,745; 08/613,207, now U.S. Pat. No.5,703,436; 08/632,322, now U.S. Pat. No.5,757,026 and 08/693,359, now U.S. Pat. No. 6,358,631 and provisional patent application Ser. Nos. 60/010,013, 60/024,001, 60/025,501, 60/046,061 and 60/053,176, each of which is also incorporated herein by reference in its entirety.

The materials that may be used as the substrate, the hole-injecting anode layer, the hole transporting layer, the electron transporting layer, the electron-injecting, metal cathode layer or the electron-injecting, non-metallic cathode layer, the protection layer, if present, the separate emissive layer, if present, or the insulating layer, if present, include the materials as disclosed in these co-pending applications.

The OLED of the present invention may be used in substantially any type of device which is comprised of an OLED, for example, in OLEDs that are incorporated into a larger display, a vehicle, a computer, a television, a printer, a large area wall, theater or stadium screen, a billboard or a sign.

This invention will now be described in detail with respect to showing how certain specific representative embodiments thereof can be made, the materials, apparatus and process steps being understood as examples that are intended to be illustrative only. In particular, the invention is not intended to be limited to the methods, materials, conditions, process parameters, apparatus and the like specifically recited herein.

AN EXAMPLE OF THE INVENTION

The procedures that were used for fabrication of Organic Light-Emitting Devices (OLEDs) were as follows:

The hole transporting material TPD and the electron transporting material $Alq_3$ were synthesized according to literature procedures, and were sublimed before use. The dopant PtOEP was purchased from Porphyrin Products, Inc., Logan, Utah, and was used as received.

OLEDs were prepared using the following procedures: The ITO/Borosilicate substrates (100 Ω/square) were cleaned by sonicating with detergent for five minutes followed by rinsing with deionized water. They were then treated twice in boiling 1,1,1-trichloroethane for two minutes. The substrates were then sonicated twice with acetone for two minutes and twice with methanol for two minutes.

The background pressure prior to deposition was normally $7\times10^{-7}$ torr or lower and the pressure during the deposition was around $5\times10^{-7}$ to $1.1\times10^{-6}$ torr.

All the chemicals were resistively heated in various tantalum boats. TPD was first deposited at a rate from one to four Å/s. The thickness was-typically controlled at 300 Å.

The electron transporting layer $Alq_3$ was doped with PtOEP.

Typically, the dopant was first vaporized with the substrates covered. After the rate of the dopant was stabilized, the host material was vaporized to the certain rate. The cover over the substrates was then opened and the host and guest were deposited at the desired concentration. The rate of dopant was normally 0.1-0.2 Å/s. The total thickness of this layer was controlled at about 450 Å.

The substrates were removed from the deposition system and masks were put directly on the substrates. The masks were made of stainless steel sheet and contain holes with diameters of 0.25, 0.5, 0.75 and 1.0 mm. The substrates were then put back into vacuum for further coating.

Magnesium and silver were co-deposited at a rate normally of 2.6 Å/s. The ratio of Mg:Ag varied from 7:1 to 12:1. The thickness of this layer was typically 500 Å. Finally, 1000 Å Ag was deposited at the rate between one to four Å/s.

The devices were characterized within five hours of fabrication. Typically electroluminescent spectra, I-V curves, and quantum yields were measured from direct front.

What is claimed is:

1. An organic light emitting device comprising a single or double heterostructure comprising an emissive layer,
    wherein the emissive layer is a charge carrying layer comprising a charge carrying material and a phosphorescent material, wherein the phosphorescent material is present at a lower concentration than the charge carrying material, and wherein the phosphorescent material is capable of capturing exciton triplet energy from the charge carrying material, and
    wherein the phosphorescent material emits phosphorescent radiation from a triplet molecular excited state when a voltage is applied across the device.

2. The device of claim 1, wherein the emissive layer is a hole transporting layer.

3. The device of claim 1, wherein the emissive layer is an electron transporting layer.

4. The device of claim 1, wherein the phosphorescent material is capable of a photoluminescent quantum yield greater than 50 percent in the solid state.

5. The device of claim 1, wherein the phosphorescent material has a phosphorescent lifetime of no longer than 10 microseconds.

6. The device of claim 1, wherein the phosphorescent material emits phosphorescent radiation from a triplet molecular excited state at room temperature.

7. The device of claim 1, wherein the phosphorescent material has the chemical structure of formula I:

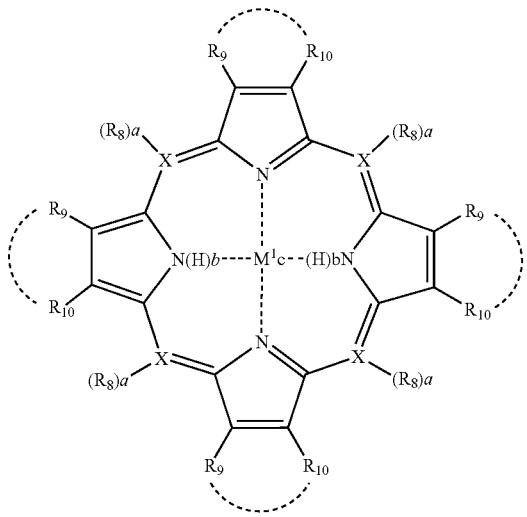

wherein X is C; $R_8$, $R_9$, and $R_{10}$ are each independently selected from the group consisting of hydrogen, alkyl, substituted alkyl, aryl and substituted aryl; $R_9$ and $R_{10}$ may be combined together to form a fused ring; M1 is Pt; a is 1; b is 0; and c is 1.

8. The device of claim 7, wherein the phosphorescent material is platinum octaethylporphine and has the chemical structure with the formula:

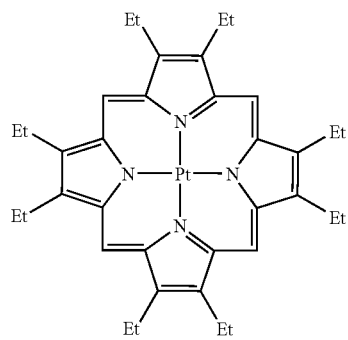

wherein Et is an ethyl group.

9. The device of claim 1, wherein the device is incorporated into an optoelectronic device.

10. The device of claim 9, wherein the optoelectronic device is incorporated into one of a vehicle, a computer, a television, a printer, a large area wall, a theater or stadium screen, a billboard, or a sign.

11. An organic light emitting device, comprising an anode, a cathode, and an emissive layer between the anode and the cathode, wherein the emissive layer comprises a phosphorescent material and a charge carrying host material, wherein the phosphorescent material is capable of a photoluminescent quantum yield greater than 50 percent in the solid state, and the phosphorescent material emits phosphorescent radiation from a triplet molecular excited state at room temperature when a voltage is applied across the organic light emitting device.

12. The device of claim 11, wherein the emissive layer is a hole transporting layer and the charge carrying host material transports holes.

13. The device of claim 11, wherein the emissive layer is an electron transporting layer and the charge carrying host material transports electrons.

14. The device of claim 11, wherein the phosphorescent material has a phosphorescent lifetime of no longer than 10 microseconds.

15. The device of claim 11, wherein the device is incorporated into an optoelectronic device.

16. The device of claim 15, wherein the optoelectronic device is incorporated into one of a vehicle, a computer, a television, a printer, a large area wall, a theater or stadium screen, a billboard, or a sign.

* * * * *